(12) United States Patent
Ramsey et al.

(10) Patent No.: US 9,139,426 B2
(45) Date of Patent: Sep. 22, 2015

(54) METHODS, SYSTEMS AND DEVICES FOR FORMING NANOCHANNELS

(75) Inventors: John Michael Ramsey, Chapel Hill, NC (US); Laurent Menard, Cary, NC (US); Valeri Gorbounov, Kingsport, TN (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 179 days.

(21) Appl. No.: 13/824,767

(22) PCT Filed: Sep. 19, 2011

(86) PCT No.: PCT/US2011/052127
§ 371 (c)(1),
(2), (4) Date: Mar. 18, 2013

(87) PCT Pub. No.: WO2012/040098
PCT Pub. Date: Mar. 29, 2012

(65) Prior Publication Data
US 2013/0195723 A1 Aug. 1, 2013

Related U.S. Application Data

(60) Provisional application No. 61/384,738, filed on Sep. 21, 2010.

(51) Int. Cl.
*B81C 1/00* (2006.01)
*B01L 3/00* (2006.01)
(Continued)

(52) U.S. Cl.
CPC ....... *B81C 1/00547* (2013.01); *B01L 3/502707* (2013.01); *B32B 3/30* (2013.01); *B81C 1/00071* (2013.01); *G01N 27/44756* (2013.01);
(Continued)

(58) Field of Classification Search
CPC .......... B01L 2200/12; B01L 2300/123; B01L 2300/16; B01L 2300/0896; B82Y 30/00; B82Y 15/00; B82Y 10/00; B82Y 40/00; B82Y 5/00; B81C 1/00071; B81C 1/0046; B81C 2201/0153; B01J 19/0093; B81B 1/002; B81B 2201/058; G03F 7/0002; H05K 3/0079
See application file for complete search history.

(56) References Cited

U.S. PATENT DOCUMENTS 6,524,456 B1 2/2003 Ramsey et al.
7,670,770 B2 3/2010 Chou et al.
(Continued)

FOREIGN PATENT DOCUMENTS

JP 2003-166934 A 6/2003
WO WO 00/02038 A1 1/2000
(Continued)

OTHER PUBLICATIONS

Chekurov et al. Nanotechnology 20 (2009) 065307 (5pp).*
(Continued)

*Primary Examiner* — Sally Merkling
(74) *Attorney, Agent, or Firm* — Myers Bigel Sibley & Sajovec, P.A.

(57) ABSTRACT

Methods of forming at least one nanochannel include: (a) providing a substrate having a thick single or a thick multi-layer overlayer; (b) milling at least one channel through the overlayer into the substrate; then (c) removing the overlayer; and (d) forming at least one nanochannel in the substrate having an average width and depth dimension that is less than about 10 nm in response to the milling and removing steps.

23 Claims, 11 Drawing Sheets

(51) Int. Cl.
*G01N 27/447* (2006.01)
*B32B 3/30* (2006.01)
*G01N 21/03* (2006.01)

(52) U.S. Cl.
CPC .... *B01L3/502761* (2013.01); *B01L 2200/0663* (2013.01); *B01L 2300/0896* (2013.01); *B81B 2201/058* (2013.01); *B81C 2201/0132* (2013.01); *G01N 2021/0346* (2013.01); *Y10T 428/24479* (2015.01); *Y10T 428/24975* (2015.01)

(56) References Cited

U.S. PATENT DOCUMENTS

| | | | |
|---|---|---|---|
| 2005/0023156 | A1 | 2/2005 | Ramsey et al. |
| 2005/0103713 | A1 | 5/2005 | Ramsey et al. |
| 2005/0196746 | A1 | 9/2005 | Xu et al. |
| 2006/0240573 | A1 | 10/2006 | Kao et al. |
| 2006/0278879 | A1 | 12/2006 | Busta |
| 2007/0192911 | A1 | 8/2007 | Xin et al. |
| 2008/0057192 | A1 | 3/2008 | Faguet |
| 2009/0115094 | A1 | 5/2009 | Chou et al. |
| 2010/0029508 | A1* | 2/2010 | Austin et al. ............ 506/16 |
| 2010/0159462 | A1* | 6/2010 | Takayama et al. .......... 435/6 |

FOREIGN PATENT DOCUMENTS

WO    WO 2007/011622 A2    1/2007
WO    WO 2008/132734 A2    11/2008

OTHER PUBLICATIONS

Abgrall et al. "Nanofluidic Devices and Their Applications", *Anal. Chem.*, 2008, 80:2326-2341.
Balducci et al. "Double-Stranded DNA Diffusion in Slitlike Nanochannels", *Macromolecules*, 2006, 39:6273-6281.
Campbell et al. "Electrophoretic manipulation of single DNA molecules in nanofabricated capillaries", *Lab Chip*, 2004, 4:225-229.
Cao et al. "Fabrication of 10 nm enclosed nanofluidic channels", *Applied Physics Letters*, 81, 174-176 (2002).
Cross et al. "Size-dependent DNA mobility in nanochannels", *Journal of Applied Physics*, 102:024701-1-024701-5; (2007).
Cui "Counterion-Hopping along the Backbone of Single-Stranded DNA in Nanometer Pores: A Mechanism for Current Conduction", *Physical Review Letters*, 98:138101, 2007.
Douville et al. "DNA linearization through confinement in nanofluidic channels", *Anal Bioanal Chem.*, 2008, 391:2395-2409.
Fan et al. "DNA Translocation in Inorganic Nanotubes", *Nano Letters*, vol. 5, No. 9, Sep. 2005, 5 pages.
Gierak et al. "Sub-5 nm FIB direct patterning of nanodevices", *Microelectronic Engineering*, vol. 84, Issue 5-8, May-Aug. 2007, 779-783.
Han et al. "Prediction of nanopattern topography using two-dimensional focused ion beam milling with beam irradiation intervals", *Microelectronic Engineering*, vol. 87, Issue 1, Jan. 2010, 1-9.
Haneveld et al. "Wet anisotropic etching for fluidic 1D nanochannels", *J. Micromech. Microeng.*, 13, 2003, S62-S66.
Holzer et al. "Three-dimensional analysis of porous $BaTiO_3$ ceramics using FIB nanotomography", *Journal of Microscopy*, vol. 216, Pt. 1, Oct. 2004, 84-95.
Huh et al. "Tuneable elastomeric nanochannels for nanofluidic manipulation", *Nature Materials*, vol. 6, Jun. 2007, 424-428.
International Preliminary Report on Patentability Corresponding to International Application No. PCT/US2011/052127; Date of Mailing: Apr. 4, 2013; 8 Pages.
International Search Report and Written Opinion Corresponding to International Application No. PCT/US2011/052127; Date of Mailing: Apr. 27, 2012; 13 Pages.
International Search Report and Written Opinion Corresponding to International Application No. PCT/US2013/025078; Date of Mailing: May 15, 2013; 12 Pages.

Kovarik et al. "Nanofluidics in Lab-on-a-Chip Devices", *Anal. Chem.*, 2009, 81:7133-7140.
Lagerqvist et al. "Fast DNA Sequencing via Transverse Electronic Transport", *Nano Letters*, vol. 6, No. 4, 2006, 779-782.
Lerman et al. "Why Does the Electrophoretic Mobility of DNA in Gels Vary with the Length of the Molecule?", *Biopolymers*, vol. 21, 995-997, 1982.
Li et al. "Focused ion beam fabrication of silicon print masters", *Nanotechnology*, 14, 2003, 220-223.
Lugstein et al. "FIB processing of silicon in the nanoscale regime", *Applied Physics A*, 76:545-548, 2003.
Maleki et al. "A nanofluidic channel with embedded transverse nanoelectrodes", *Nanotechnology*, 20:105302; 2009.
Menard et al. "Analysis of Single DNA Molecules Translocating Through Nanochannels Fabricated in $SiO_2$", *Twelfth International Conference on Miniaturized Systems for Chemistry and Life Sciences*, Oct. 12-16, 2008, San Diego, California, 4 pages.
Menard et al, "Fabrication of sub-5 nm nanochannels in insulating substrates using focused ion beam milling", *Nano Letters*, 2011, vol. 11, No. 2, 512-617.
Menard Jr. et al, "DNA Transport Characteristics in Focused Beam-Milled Nanofluidic Devices", *2009 Annual Meeting of the American Electrophoresis Society (AES)*, Nov. 10, 2009, Retrieved from the internet at URL http://aiche.confex.com/aiche/2009/webprogram/Paaper160572.html.
Mijatovic et al. "Technologies for nanofluidic systems: *top-down vs. bottom-up*—a review", *Lab Chip*, 2005, 5, 492-500.
Nakayama et al. "Stability and Schottky barrier of silicides: First-principles study", *Microelectronic Engineering*, vol. 86, Issues 7-9, Jul.-Sep. 2009, pp. 1718-1721.
Nikoobakht, "A Scalable Platform for Integrating Horizontal Nanochannels with Known Registries to Microchannels", *Chem. Mater.*, 2009, 21, 27-32.
Orloff et al. "Fundamental limits to imaging resolution for focused ion beams", *Journal of Vacuum Science & Technology B*, 14, 3759-3763 (1996).
Perry et al. "Review of fabrication of nanochannels for single phase liquid flow", *Microfluid Nanofluid*, 2006, 2:185-193.
Ramsey et al. 2007 Progress Report, National Human Genome Research Institute, National Institutes of Health, 3 pages (2007), Applicant Redacted Version for USPTO IDS submission with appended paragraph of PHS (NHGRI) FOIA implementing guidelines including progress reports and withholding policy (5 pages).
Randolph et al. "Focused, Nanoscale Electron-Beam-Induced Deposition and Etching", *Critical Reviews in Solid State and Materials Sciences*, 31:3, 55-89, 2006.
Reisner et al. "Nanoconfinement-Enhanced Conformational Response of Single DNA Molecules to Changes in Ionic Environment", *Physical Review Letters*, 99, 058302, 2007.
Reisner et al. "Statics and Dynamics of Single DNA Molecules Confined in Nanochannels", *Physical Review Letters*, 94, 196101, 2005.
Riehn et al. "Restriction mapping in nanofluidic devices", *PNAS*, Jul. 19, 2005, vol. 102, No. 29, 10012-10016.
Salieb-Beugelaar et al. "Electrophoretic separation of DNA in gels and nanostructures", *Lab Chip*, 2009, 9:2508-2523.
Salieb-Beugelaar et al. "Field-Dependent DNA Mobility in 20 nm High Nanoslits", *Nano Letters*, vol. 8, No. 7, Jul. 2008.
Schoch "Transport phenomena in nanofluidics", *Reviews of Modern Physics*, vol. 80, Jul.-Sep. 2008, 839-883.
Striemer et al. "Charge- and size-based separation of macromolecules using ultrathin silicon membranes", *Nature*, vol. 445, Feb. 15, 2007, 749-753.
Strychalski et al. "Diffusion of DNA in Nanoslits", *Macromolecules*, 2008, 41:7716-7721.
Tong et al. "Silicon Nitride Nanosieve Membrane", *Nano Letters*, 2004, vol. 4, No. 2, 283-287.
Tseng "Recent developments in micromilling using focused ion beam technology", *Journal of Micromechanics and Microengineering*, 14:R15-R34, 2004.

(56) References Cited

OTHER PUBLICATIONS

Volkmuth et al. "DNA electrophoresis in microlithographic arrays", *Nature*, vol. 358, Aug. 13, 1992, 600-602.

Wang et al. "Manipulating DNA molecules in nanofluidic channels", *Microfluid Nanofluid*, 2:85-88; 2006.

Wang et al. "Single-molecule studies of repressor-DNA interactions show long-range interactions", PNAS, Jul. 12, 2005, vol. 102, No. 28, 9796-9801.

Xu et al. "Wide-spectrum, ultrasensitive fluidic sensors with amplification from both fluidic circuits and metal oxide semiconductor field effect transistors", *Applied Physics Letters*, 91:013901, 2007.

Yuan et al. "Electrokinetic transport and separations in fluidic nanochannels", *Electrophoresis*, 2007, 28:595-610.

Zwolak "Electronic Signature of DNA Nucleotides via Transverse Transport", *Nano Letters*, vol. 5, No. 3, 2005, 421-424.

Chekurov et al., The fabrication of silicon nanostructures by local gallium implantation and cryogenic deep reactive ion etching, Nanotechnology, 2009, pp. 1-5, vol. 20.

Giannuzzi et al., 2keV Ga+ FIB Milling for Reducing Amorphous Damage in Silicon, Microsc Microanal. 2005, pp. 828-829, vol. 11, Suppl. 2.

Menard et al., Fabrication of Sub-5 nm Nanochannels in Insulating Substrates Using Focused Ion Beam Milling, Nano Lett., 2011, pp. 512-517, vol. 11.

Reisner et al., DNA confinement in nanochannels: physics and biological applications, Rep. Prop. Phys., 2012, pp. 1-34 pages, vol. 75.

\* cited by examiner

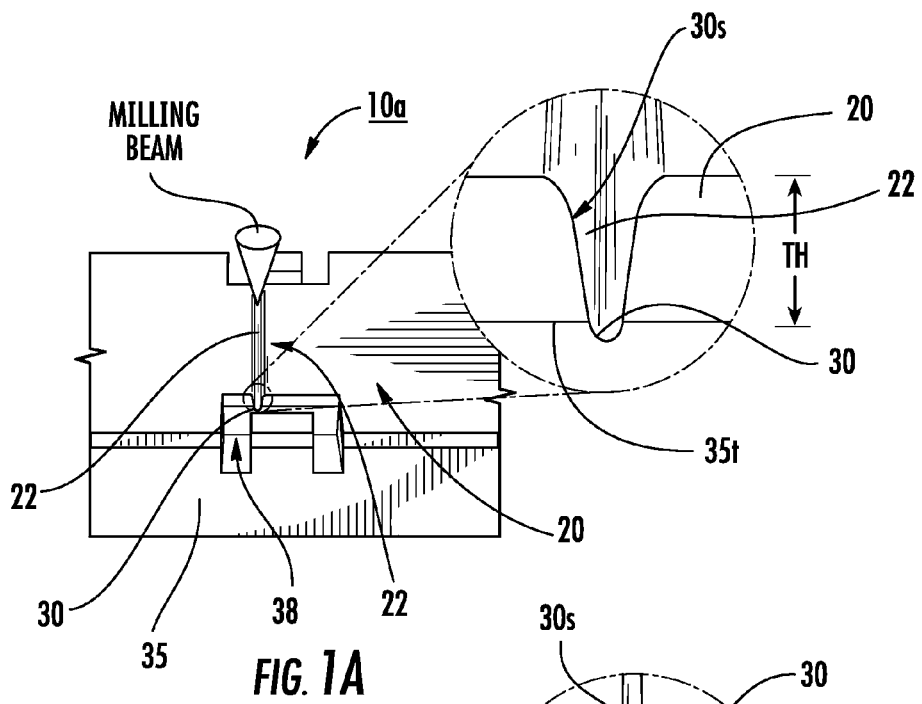
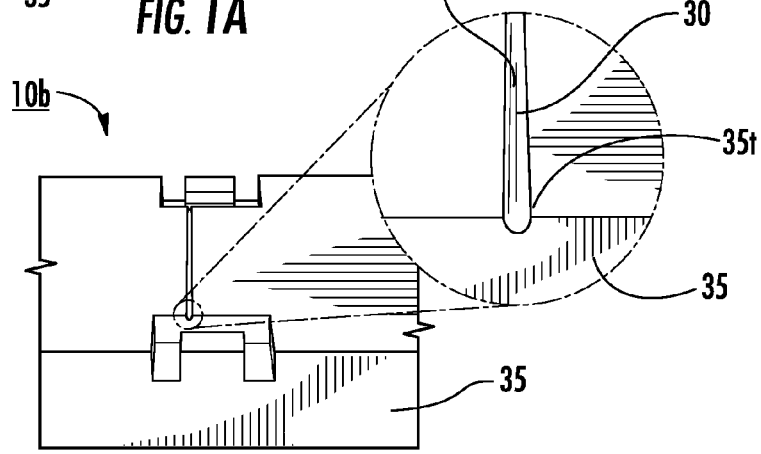
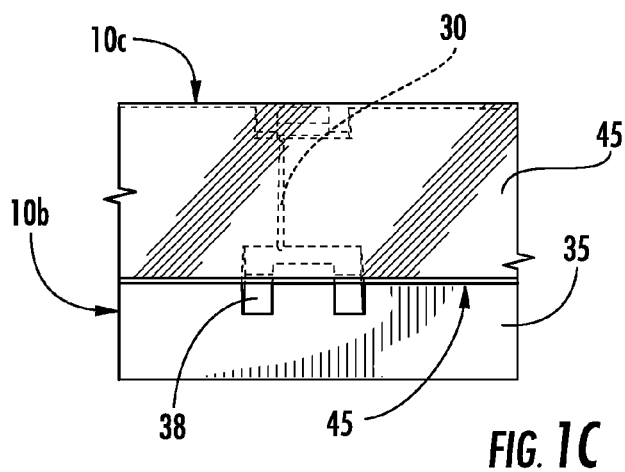

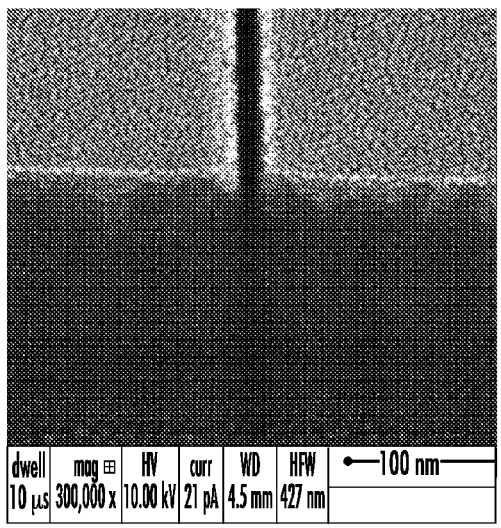
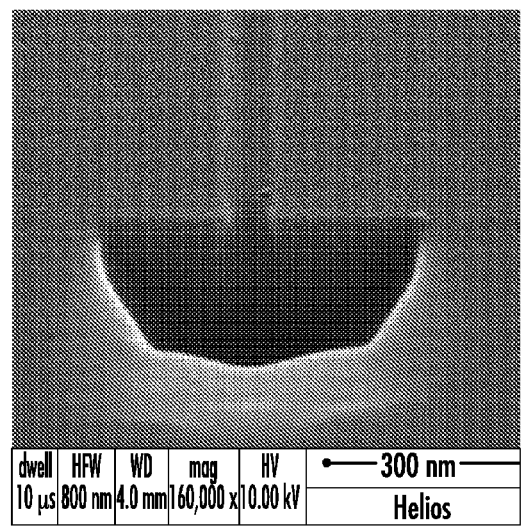
FIG. 12A
FIG. 12B

METHODS, SYSTEMS AND DEVICES FOR FORMING NANOCHANNELS

STATEMENT OF FEDERAL SUPPORT

This invention was made with government support under Grant Nos. HG002647 awarded by the National Institutes of Health. The government has certain rights in this invention.

RELATED APPLICATIONS

This application is a 35 USC §371 national phase application of PCT/US2011/052127, International Filing Date Sep. 19, 2011, which claims the benefit of and priority to U.S. Provisional Application Ser. No. 61/384,738, filed Sep. 21, 2010, the contents of which are hereby incorporated by reference as if recited in full herein.

FIELD OF THE INVENTION

This invention relates to fluidics and microelectronic devices using nanochannels.

BACKGROUND OF THE INVENTION

There has been considerable recent interest in the incorporation of nanoscale components in lab-on-a-chip fluidic devices. This interest owes its origin to several advantages (and differences that may be advantageously leveraged) in moving from the micron scale to the nanoscale. These differences include, for example, double-layer overlap (DLO) and its effect on electro-osmosis and charge permselectivity, localized enhancement of electric fields, higher surface to volume ratios, confinement effects on large synthetic and biopolymers, and the emerging importance of entropic effects. See, e.g., Yuan et al., *Electrophoresis* 2007, 28, 595-610; Schoch et al., *Rev. Mod. Phys.* 2008, 80, 839-883; and Kovarik et al., *Anal. Chem.* 2009, 81, 7133-7140. Historic examples of nanoscale devices include the use of porous media and gels in chromatographic separations and filtration membranes with nanoscale pores. See, e.g., Lerman et al., *Biopolymers* 1982, 21, 995-997; and Tong et al., *M. Nano Lett.* 2004, 4, 283-287. Recent efforts, however, have been focused on engineering geometrically well-defined conduits for fluid and analyte transport and seamlessly integrating them into devices. See, e.g., Volkmuth et al., *Nature* 1992, 358, 600-602; and Striemer et al., *Nature* 2007, 445, 749-753. The advantage of such regular structures is the relative simplicity of pressure and field gradients, fluid flow, and molecular motion contained within, in contrast to these properties in more tortuous networks. The capability to define, characterize, and easily model these systems can allow a better understandings of separation mechanisms and single molecule physics, for example. See, e.g., Volkmuth et al., *Nature* 1992, 358, 600-602; Reisner et al., *Phys. Rev. Lett.* 2005, 94, 196101; and Salieb-Beugelaar et al., *Lab Chip* 2009, 9, 2508-2523.

A number of fabrication tools have been brought to bear on the challenge of fabricating nanochannels. The methods suitable for nanochannel fabrication have been extensively reviewed. See, e.g., Douville et al., *Anal. Bioanal. Chem.* 2008, 391, 2395-2409; Mijatovic et al., *A. Lab Chip* 2005, 5, 492-500; Perry et al., *Microfluid. Nanofluid.* 2006, 2, 185-193; and Abgrall et al., *Anal. Chem.* 2008, 80, 2326-2341. Photolithography has been used to fabricate "nanoslits"—features with widths defined by the resolution limits of photolithography (i.e. usually several hundred nm to microns) and nanometer-scale depths defined by short duration wet or dry etching techniques. See, e.g., Cross et al., *J. Appl. Phys.* 2007, 102, 024701; Balducci et al., *Macromolecules* 2006, 39, 6273-6281; and Salieb-Beugelaar et al., *Nano Lett.* 2008, 8, 1785-1790. Nanoimprint lithography has been shown capable of producing nanofluidic channels that are as small as 10 nm wide. See, e.g., Cao et al., *Appl. Phys. Lett.* 2002, 81, 174-176. Electron beam lithography (EBL) has been used to pattern nanochannels for use in DNA extension studies with dimensions as small as 50 nm. See, e.g., Reisner et al., *Phys. Rev. Lett.* 2007, 99, 058302. Single DNA molecules have also been studied in focused ion beam (FIB) milled nanochannels on the order of 100 nm. See, e.g., Campbell et al., *Lab Chip* 2004, 4, 225-229; and Riehn et al., *Proc. Natl. Acad. Sci*, USA 2005, 102, 10012-10016. Various templating and molding strategies have also been used to generate nanochannels for nanofluidic studies in the 50-100 nm range. See, e.g., Fan et al., *Nano Lett.* 2005, 5, 1633-1637; and Huh et al., S. *Nat. Mater.* 2007, 6, 424-428. Ultimate dimensions for templating strategies have alleged to be able to extend below 10 nm, although channels this small have not been demonstrated as platforms in fluidic experiments. See, e.g., Nikoobakht, B., *Chem. Mater.* 2009, 21, 27-32.

SUMMARY OF EMBODIMENTS OF THE INVENTION

Embodiments of the invention are directed to methods of forming at least one nanochannel. The methods can include: (a) providing a substrate having a thick single or a thick multi-layer overlayer; (b) milling at least one channel through the overlayer into the substrate; then (c) removing the overlayer; and (d) forming at least one nanochannel in the substrate having an average width and depth dimension that is less than about 10 nm in response to the milling and removing steps.

In some embodiments, the forming step is carried out to form a plurality of nanochannels in the substrate, the nanochannels having a width and/or depth that is between about 0.5 nm to about 10 nm, such as less than about 5 nm (e.g., about 3 nm). In some embodiments, the nanochannels can have a width and/or depth that is less than about 1 nm. In particular embodiments, the forming step can be carried out to form a plurality of nanochannels in the substrate, the nanochannels having a depth that is between about 0.5 nm to about 10 nm, which can be between 0.5 nm to about 3 nm, and a width that is between about 0.5 nm to about 5 nm, such as between about 1 nm to about 3 nm.

Yet other embodiments are directed to a substrate having a plurality of spaced apart, side-by-side nanochannels produced by the above-defined method.

A cover can be (hermetically and/or fluidically) sealably attached to the substrate and a (single) molecule of stained DNA can reside in at least one nanochannel.

Other embodiments are directed to devices for analyzing nucleic acids. The devices include a nanofluidic chip comprising a plurality of nanochannels having a depth that is between about 1 nm to about 5 nm, and a width that is between about 1 nm to about 5 nm. The nanochannels have a smooth inner surface and the nanochannels have implanted $Ga^+$ ions.

The nanochannels can include respective single molecule DNA for fluorescent analysis.

Yet other embodiments are directed to a mold for imprint nanolithography fabrication of microelectronic devices. The mold includes a planar substrate comprising a plurality of nanochannels having a depth that is between about 0.5 nm to about 10 nm, such as between about 0.5 nm to about 5 nm, and a width that is between about 0.5 nm to about 10 nm, such as between about 0.5 nm to about 5 nm. The nanochannels can have a smooth inner surface. The nanochannels may have implanted $Ga^+$ ions (or traces thereof if removed by appropriate processing).

Still other embodiments are directed to fabrication assemblies for fabricating fluidic nanochannels. The assemblies include: (a) a substantially planar substrate having a thickness between about 30 nm to about 5 mm; and (b) a thick metallic film overlayer having a thickness that is between about 50 nm to about 500 nm attached to the substrate.

Another aspect is directed to a method of evaluating DNA. The method includes obtaining a time-series of images of a single molecule of fluorescently-stained λ-phage DNA in a nanochannel having a depth dimension that is between about 0.5 nm to about 10 nm, typically between about 1 nm to about 5 nm (e.g., about 3 nm).

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIG. 1A is a three-dimensional perspective schematic view of an exemplary substrate with an overlayer with a channel formed though the overlayer into the substrate according to embodiments of the present invention.

FIG. 1B illustrates the device of FIG. 1A with the overlayer removed according to embodiments of the present invention.

FIG. 1C illustrates the device of FIG. 1B with a cover sealably attached to the device according to some embodiments of the present invention.

FIGS. 6a-6c are before Cr overlayer removal and FIGS. 6d-6f are after Cr removal.

FIGS. 9e and 9f show the nanochannel milled directly into the substrate while FIGS. 9a-9d show channels milled through a 150 nm Al layer. FIGS. 9a and 9c are before Al removal and FIGS. 9b and 9d are after Al removal.

FIG. 10a illustrates the feature milled directly into the substrate and FIG. 10b illustrates the feature milled into the substrate via a 150 nm thick Al film, followed by removal of the Al film by wet chemical etching.

FIG. 11a illustrates the nanochannel in a stretched configuration and FIG. 11b illustrates the nanochannel in a nonstretched configuration (specimens are tilted about 52 degrees with respect to the electron beam).

FIGS. 12a and 12b are SEM images of milled nanochannels subjected to a subsequent high temperature heat treatment. FIG. 12b illustrates the shape adjustment of the nanochannel into a shallow (slit-like) configuration.

DESCRIPTION OF EMBODIMENTS OF THE INVENTION

Figure 2:
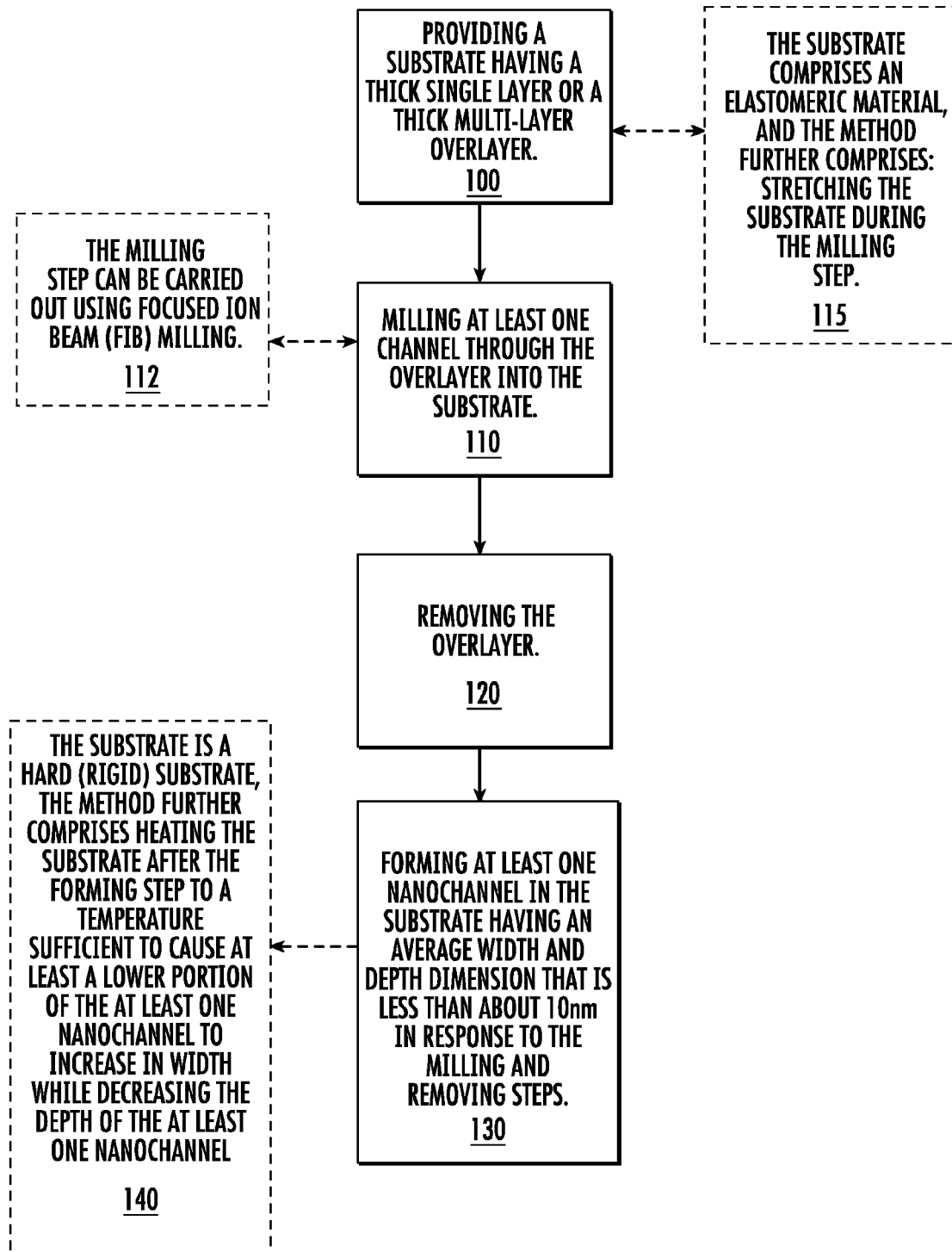
FIG. 2 is a flow chart of exemplary operations that can be used to form nanochannels according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. Well-known functions or constructions may not be described in detail for brevity and/or clarity.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Generally stated, embodiments of the application provide techniques using milling to fabricate nanochannels with primary (sometimes described as "critical") dimensions. The term "milling" refers to any process that forms channels using a charged particle or particles. Thus, while some examples are described herein with respect to an FIB milling process. Other milling processes that may be used include $Ar^+$ ion beams, proton beams, He ion beams, $Ga^+$, $In^+$, $C_{60}^+$, and electron beam milling. The term "implanted projectiles" refers to the particles implanted in the substrate nanochannels in response to the milling process (based on the type of beam used to form the nanochannel). In the resulting device used to analyze (fluidic) samples, the implanted projectiles may be present in a trace amount (detectable with SEM or other evaluation methods), present in larger amounts or removed (e.g., via known subsequent processing techniques).

Another mode of operation is to alternate charged particle milling with charged particle induced deposition processes that allows redeposition of masking material during the milling process. The redeposition of masking materials will allow for a renewal of the masking material during the etching process enabling greater aspect ratio nanochannels to be produced. The deposition of solid phase materials using focused particle beams and volatile precursor molecules is a well-established technique. (see S. J. Randolph, et al., Crit. Rev. Solid State Mat. Sci., 2006, 31, 55-89, the contents of which are hereby incorporated by reference as if recited in full herein.) A broad range of metals, insulators, and semiconductor materials can be deposited using these technique including Cr, Pt, Si, $SiO_2$. The redeposition process may be particularly important when milling the narrowest high-aspect ratio channels. These channels can be milled by rastering the charged particle beam along a line. Precursor gas of the deposited material can be injected at appropriate intervals during the beam rastering to achieve the desired nanochannel dimensions.

The term "nanochannels" refers to an elongate channel with sidewalls and a floor, sometimes also referred to as a "trench". The nanochannels can be formed into a solid substrate to have an open top surface and a closed bottom surface with the sidewalls extending therebetween. A cover may be used to seal or otherwise close the upper surface of the nanochannel. The term "primary dimension" in the singular and plural refers to a width and/or depth dimension. The primary dimensions are both typically below about 10 nm, including about 5 nm or less (on average or at a maxima). In some embodiments, the depth and/or width can be about 3 nm or less, e.g., about 1 nm. In some embodiments, the depth is between about 1 nm to about 10 nm (on average or at a maxima) and the width is the same or larger (e.g., between about 2-10 times larger than the depth dimension, again either measured on average or as a maxima). The length of the nanochannels can vary typically according to end application. However, in some embodiments the nanochannels can have a relatively short length such as about 100 nm, but typically between about 10 microns to 100 microns. In other embodiments, the nanochannels can be longer, such as between about 0.5-12 inches (particularly when using stitching or continuous precisely controlled movements of a sample stage while milling), although more typically between about 0.5-2 inches.

The nanochannels can be configured with an aspect ratio of about 1 (e.g., the average width and average depth are substantially the same or do not vary more than about 20%). In other embodiments, the process can be carried out to form nanochannels with different aspect ratios, typically with the width dimension being 2-10 times greater than the depth dimension, e.g., such as an AR of about 1:3 (H (depth dimension):W). In some embodiments, the process can be carried out to form nanochannels with aspects greater than 1, but less than 10.

As shown in FIG. 1A, a device 10a includes at least one overlayer 20 that is attached to an underlying substrate 35 with at least one nanochannel 30 formed in the substrate 35. This device 10a can be described as a fabrication assembly as it is in a fabrication configuration which is suitable for forming the channels 30 using a milling apparatus. This fabrication assembly/device 10a can be held on a moving platform or mounting structure to form the patterned channel configuration and/or the probe associated with the milling device/apparatus can move relative to the (upper surface of) the assembly 10a.

As shown in FIG. 1B, after the nanochannel 30 is formed into the substrate 35 through the overlayer 20, the overlayer 20 is removed to yield a device 10b (e.g., chip) without the overlayer 20 but with the substrate 35 and the at least one nanochannel 30.

The channels 30 can have sidewalls 30s that taper inwardly as they travel closer to the bottom of a respective channel 30. The channels 30 are typically substantially upright, such as between about 0-15 degrees from vertical).

The overlayer 20 can be attached to the substrate 35 in any suitable manner including, for example, adhesive, bonding, ultrasonic welding, brazing, sputter deposition, evaporative deposition, mechanical (e.g., clamped), and the like and has a thickness "TH". Typically, the overlayer 20 is bonded to the substrate 35 in a manner that does not alter (at least in any significant manner) the surface chemistry of the substrate.

The overlayer 20 can be removed in any suitable manner including electrical, chemical and mechanical means. The removal method may be selected based on the manner in which the overlayer 20 is attached to the substrate, or the material of the substrate and/or overlayer, and the like. Examples of removal methods include, for example, chemical etching, peeling, optical (light), heating, pressurized liquids and the like.

As shown in FIG. 1C, a finished device 10c with a cover 45 such as a coverplate can be sealably attached to the upper surface 35t of the substrate 35 (of the device 10b) with the at least one nanochannel 30. In particular embodiments, the devices 10b can be sealed with a glass or quartz cover using fusion bonding or anodic bonding or using a PDMS-coated glass coverslip that reversibly seals the device (typically followed by heating to irreversibly seal the device). However, other cover configurations/materials and/or seal types/processes can be used.

Optionally, prior to the attachment of the overlayer 20 and/or after formation of the nanochannel and removal of the overlayer 20, a microchannel 38 (or channels) can be formed into the substrate to be in communication with one or more nanochannels 30 using conventional techniques including, for example, FIB milling, photolithography or etching techniques. This embodiment may be particularly suitable for biosample analysis. FIG. 1A shows a schematic where the objective is to form a nanochannel feature that connects two spatially separated microchannels 38. In some embodiments, the microchannels 38 can be formed using photolithographic patterning of a photoresist, followed by wet chemical etching. Photolithographically patterned channels could also be etched using dry etching techniques such as reactive ion etching (RIE) or deep reactive ion etching (DRIE). The larger channel features could also be formed using FIB milling procedures. The nanochannel feature would then be formed using the steps outlined in FIG. 1A.

Figure 3A:
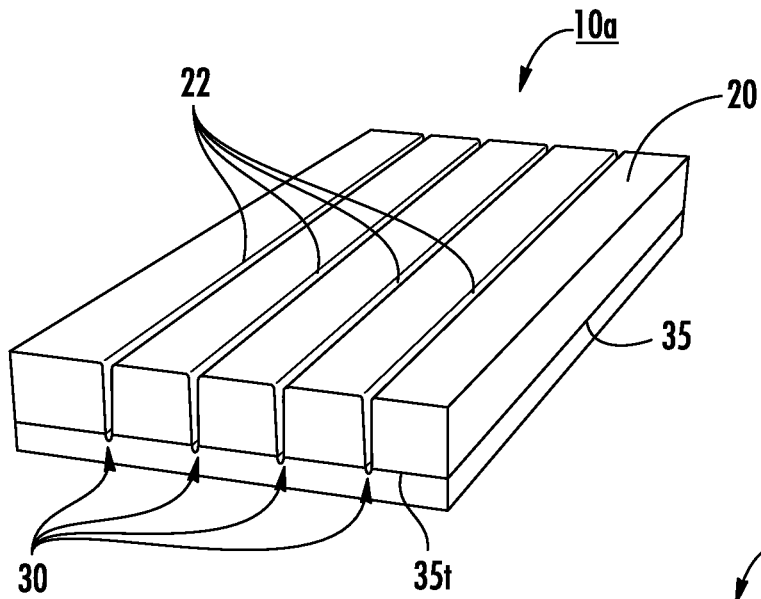
FIG. 3A is a side perspective view of an exemplary substrate and overlayer assembly according to embodiments of the present invention.
Figure 3B:
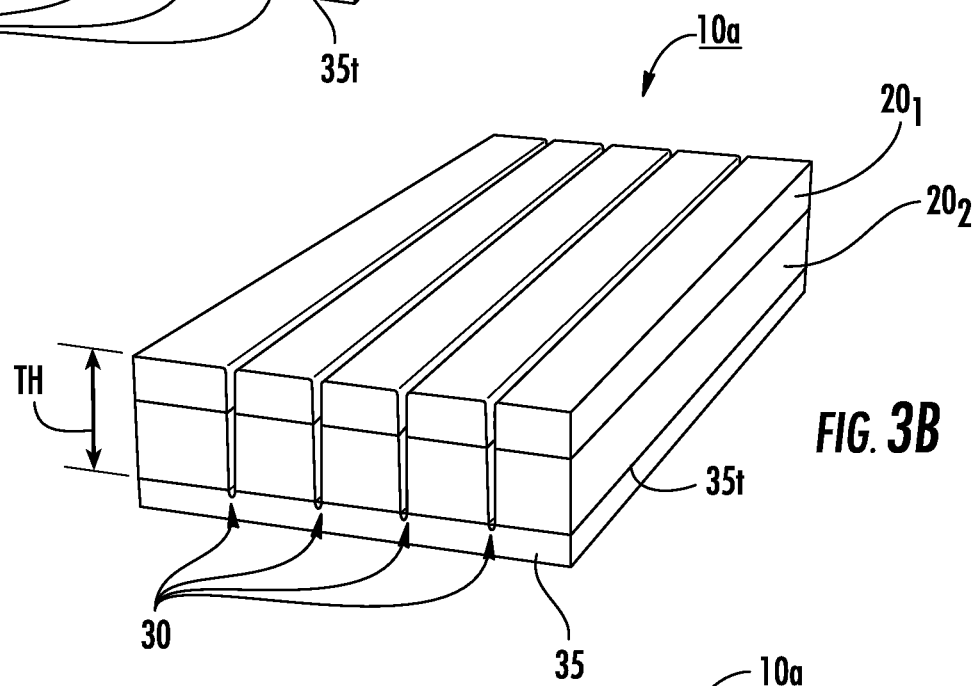
FIG. 3B is a side perspective view of another exemplary substrate and overlayer assembly according to embodiments of the present invention.

The substrate 35 can be hard (e.g., substantially rigid) or soft. The term "soft" refers to a material that is flexible, elastomeric, stretchable, plastic and/or polymeric. The substrate 35 can comprise a combination of hard and soft materials. The substrate 35 can be a substantially planar single layer of a monolithic material as shown in FIG. 3A. The substrate 35 can be a substantially planar multi-layer structure with a plurality of laminated or otherwise securely attached stacked layers as shown in FIG. 3B. Although shown as two layers $20_1, 20_2$, three or more layers may be used, e.g., 3, 4, 5, 6, 7, 8, 9 and even, in some embodiments, 10 or more.

Figure 4A:
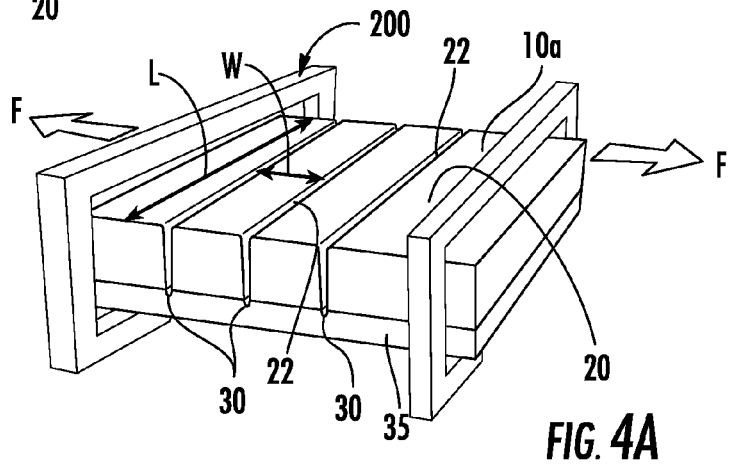
FIG. 4A is a perspective schematic illustration of a flexible substrate held in a stretched configuration for a milling process according to embodiments of the present invention.
Figure 4B:
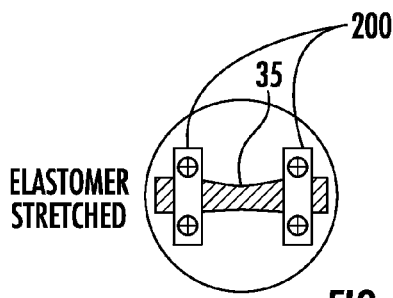
FIG. 4B illustrates the material in a stretched configuration.
Figure 4C:
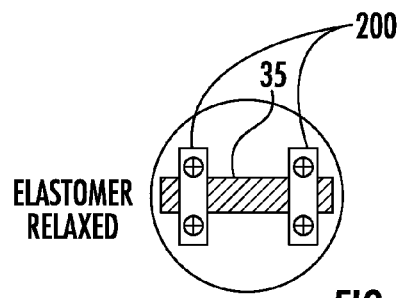
FIG. 4C illustrates the device of FIG. 4B in a relaxed configuration.

Examples of hard materials include, but are not limited to, substrates comprising one or combinations of: glass, quartz, silicon, and silicon nitride. The soft materials can have a low Young's Modulus value. For example, elastomers and harder plastics and/or polymers can have a range between about 0.1-3000 MPa. Examples of soft materials include, but are not limited to, polydimethylsiloxane (PDMS), polymethylmethacrylate (PMMA), and polyurethane.

Where soft (e.g., at least partially pliable or flexible) materials are used, the substrate 35 can be stretched during the milling step, then subsequently released to relax the substrate and reduce the channel width. The stretching can be carried out to stretch the material between about 10-30%, typically about 20%. The channels 30 can be formed with a first width dimension that reduces at least 10% when the material is relaxed to a non-stretched state (typically reduced about 15-20% in the nanochannel lateral or width dimension). During the stretching, the nanochannels 30 can be oriented such that the channel length and width are substantially perpendicular and parallel to the stretch direction, respectively. FIG. 4A illustrates a clamping mechanism 200 that can be used to stretch the soft substrate with the overlayer 10a during a milling process. As shown, the forces are applied to stretch the device 10a in (parallel to) the "W" direction with the channel 30 lengths oriented substantially perpendicular to the stretch direction. FIG. 4B illustrates the substrate 35 (and overlayer) in a stretched configuration and FIG. 4C illustrates the substrate 35 (and overlayer) in a relaxed configuration.

The overlayer 20 is a thick overlayer. The term "thick" with reference to the overlayer 20 means that the overlayer is at least 10× the thickness of the depth and/or width of the nanochannel 30. Typically, the overlayer 20 has a thickness that is between about 50-500× the depth and/or width of the nanochannel 30. The overlayer 20 can be a single monolithic material layer as shown in FIG. 1A or may be a plurality of stacked attached layers $20_1, 20_2$ as shown in FIG. 3B. The overlayer 20 (e.g., the single or multi-layer structure) can have a thickness "TH" (FIG. 3B) that is at least 50 nm, typically between about 50 nm to about 500 nm, and more typically between about 100 nm to about 400 nm.

The overlayer 20 can be conductive and configured to provide a desired low sputtering rate. The low sputtering rate is typically less than about 1.0 $\mu m^3/nC$, and more typically about 0.5 $\mu m^3/nC$ or less, such as, for example, about 0.10 $\mu m^3/nC$, about 0.23 $\mu m^3/nC$, and about 0.30 $\mu m^3/nC$, For a single monolithic overlayer structure, the overlayer can be metallic, such as a layer comprising aluminum. The overlayer 20 can be configured so that it is non-reactive with the substrate upper surface. Where multi-layer overlayer structures $20_1, 20_2$ are used (FIG. 3B), the layer $20_2$ attached to the substrate 35 can be non-reactive while another layer may be reactive or comprise a different material.

Figure 3C:
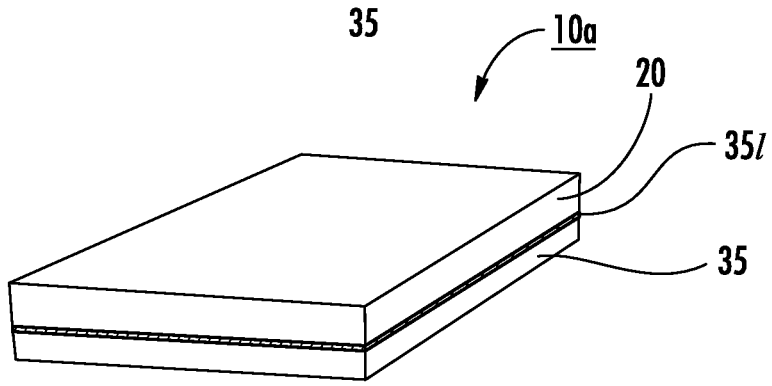
FIG. 3C is a side perspective view of yet another exemplary substrate and overlayer configuration according to embodiments of the present invention.

In some embodiments, the overlayer 20 can be insulating and the substrate 35 can be conductive. Alternatively, as shown in FIG. 3C, the device 10a can include an insulating overlayer 20 with a thin conductive layer 35l on the substrate 35 (e.g., the substrate 35 man be thicker than the thin conductive layer 35l, typically at least 10× the thickness of the thin conductive layer).

In some embodiments, the thick (e.g., greater than about 100 nm) overlayer 20 can comprise a conductive material such as a metal film. The conductive overlayer 20 can serve one or more purposes. For example, it can allow the efficient conductance of charge in the case where the underlying substrate 35 being patterned is electrically insulating. Also or alternatively, the overlayer 20 can act to partially mask the ion beam as the channel 22 is milled progressively deeper. Also or additionally, it can protect the substrate's top surface 35t (FIG. 1A) from redeposition of material and structural deformations typically observed along the edges of features milled directly into substrates. See, e.g., Lugstein et al., *Appl. Phys. A* 2003, 76, 545-548.

The use of thin metal films (on the order of a few nanometers) is believed to be a common procedure in FIB milling of insulating substrates. In these cases, the metal film serves the sole purpose of dissipating charge that would otherwise accumulate on the insulating substrate, limiting milling efficiency and spatial resolution. A common metal for this use is gold, since it can be rapidly deposited on the substrate using either sputtering or evaporative techniques and easily removed by dipping the coated substrate in aqua regia. In contrast, embodiments of the invention propose the use of thick conductive (metal) films as overlayers that exhibit low sputter rates for the ion beam used for milling (30 keV $Ga^+$ ions). Examples of thick films include films that comprise one or more of Cr, Pt, and Al which exhibit sputter rates of about 0.10, about 0.23, and about 0.30 $\mu m^3/nC$ respectively, compared to a sputter rate of 1.50 $nm^3/nC$ for Au. See, e.g., Orloff et al., *J. Vac. Sci. Technol. B* 1996, 14, 3759-3763. These lower sputter rates translate into more effective masking and smaller ultimate channel dimensions. The use of thick metal films is also beneficial for milling nanoscale channels in semiconducting substrates such as Si, which conduct charge sufficiently well that metal films are not necessary solely for charge dissipation. The benefits include smaller critical dimensions, smoother channel walls, and a high quality top surface suitable for bonding of a coverplate.

As shown in FIG. 1A, a channel 22 is milled through the overlayer 20 until it penetrates a prescribed depth into the substrate material 35. As shown in FIG. 1B, the overlayer 20 is then removed, leaving a nanochannel 30 with smooth surfaces. In some embodiments, the nanochannel 30 depth and/or width dimensions can range from about 10 nm down to about 0.5 nm. For example, one or both of the primary dimensions can be about 3 nm. It is believed that optimized homebuilt FIB systems have been reported with beam profiles down to 5 nm (see e.g., Gierak et al., Microelectron. Eng, 2007, 84, 779-783). This may allow smaller features to be created. Further, according to embodiments of the invention, it is contemplated that the described methods, systems and devices should allow the generation of features smaller than the particle beam profile of any instrument, e.g., a FIB with a sub-state-of-the-art beam profile of about 15 nm may be able to make a 10-nm feature. In particular embodiments, the nanochannels 30 can have lateral dimensions below 10 nm, typically about 5 nm or less, and in some embodiments, the width or lateral dimension is about 10 nm or less. In particular embodiments, the width or lateral dimension can be about 5 nm or less (e.g., about 4 nm, about 3 nm or about 2 nm (average)) and the depth dimension (average) is about 3 nm or less, such as about 1 nm or less. In some embodiments, the milled channel profile 22 decreases as the depth through the thick overlayer 20 increases due to several characteristics of some milling processes: the Gaussian-like beam profile, the sputtering yield dependence on the angle of incidence (self-focusing), and the redeposition of material. See, e.g., Tseng, A. A. *J. Micromech. Microeng.* 2004, 14, R15-R34; and Han et al., *Microelectron. Eng.* 2010, 87, 1-9.

FIG. 2 illustrates exemplary operations that can be used to form a device with nanochannels according to embodiments of the invention. A substrate having a thick single or a thick multi-layer overlayer is provided (block 100). At least one channel is milled through the overlayer into the substrate (block 110). The overlayer is then removed (block 120). At least one nanochannel having an average width and depth dimension that is less than about 10 nm is formed in the substrate in response to the milling step and removing steps (block 130).

Sealed nanochannels with an aspect ratio (depth:width) of 1 for use in single molecule studies of DNA transport dynamics with channel widths below 10 nm, e.g., below about 5 nm.

In some embodiments, the average width and depth dimensions are below about 10 nm, and may be below about 5 nm (e.g., which can be between about 0.5 nm to about 10 nm). In particular embodiments, the depth is about or below 1 nm and the width is less than about 5 nm (e.g., an AR (H:W) of about 1:1, about 1:2, about 1:3, about 1:4, about 1:5, about 1:6, about 1:7; about 1:8, and the like.

The milling step can be carried out using focused ion beam (FIB) milling (block 112). It is noted that, given the direct-write nature of FIB milling, the nanochannels can be easily interfaced to microchannels 38 (FIGS. 1A-1C) prepared using standard photolithography and wet etching methods.

In some embodiments, the substrate comprises an elastomeric material and the method can include stretching the substrate during the milling step (block 115).

In some embodiments, the substrate is a hard material and the method can further comprise heating the substrate after the forming step to a temperature sufficient to cause at least a lower portion of the at least one nanochannel to increase in width while decreasing the depth of the at least one nanochannel (block 140). For example, in some substrates, such as, for example, glass substrates, the implantation of ions from the charged particle(s) used for the milling process (e.g., FIB source) can lower the annealing point local to a milled nanochannel. Subsequent high temperature treatments can be carried out to allow this material to flow while remaining confined by the neighboring non-implanted substrate material, resulting in the formation of an extremely smooth nanochannel.

In one particular example, the substrate can comprise quartz. The milling step can be carried out using focused ion beam (FIB) milling configured to deposit $Ga^+$ ions in the quartz proximate the nanochannel. The method can further include heating the substrate to a temperature between about 850 degrees Celsius but less than 1200 degrees Celsius to cause the quartz proximate the at least one nanochannel to flow within a region associated with the $Ga^+$ ions to create a respective nanochannel having a wider channel dimension and a more shallow depth dimension.

In some embodiments, the nanoscale channels 30 in the substrate 35 can be characterized by one or more of: (a) an easy to apply selectable (e.g., variable) aspect ratio (height: width); (b) smooth walls; and (c) amenability to engineered surface chemistry. The roughness of the inner surface of the channel and/or the upper surface of the substrate proximate the channel (channel edges) can be smooth with low surface roughness. In some embodiments, the surface can have a roughness measurement of between about 300-800 pm root-mean-square (RMS) roughness. The relatively smooth surface can allow for longer use in fluidic testing or analysis over Si or glass nanochannels fabricated using other technologies.

Figure 5:
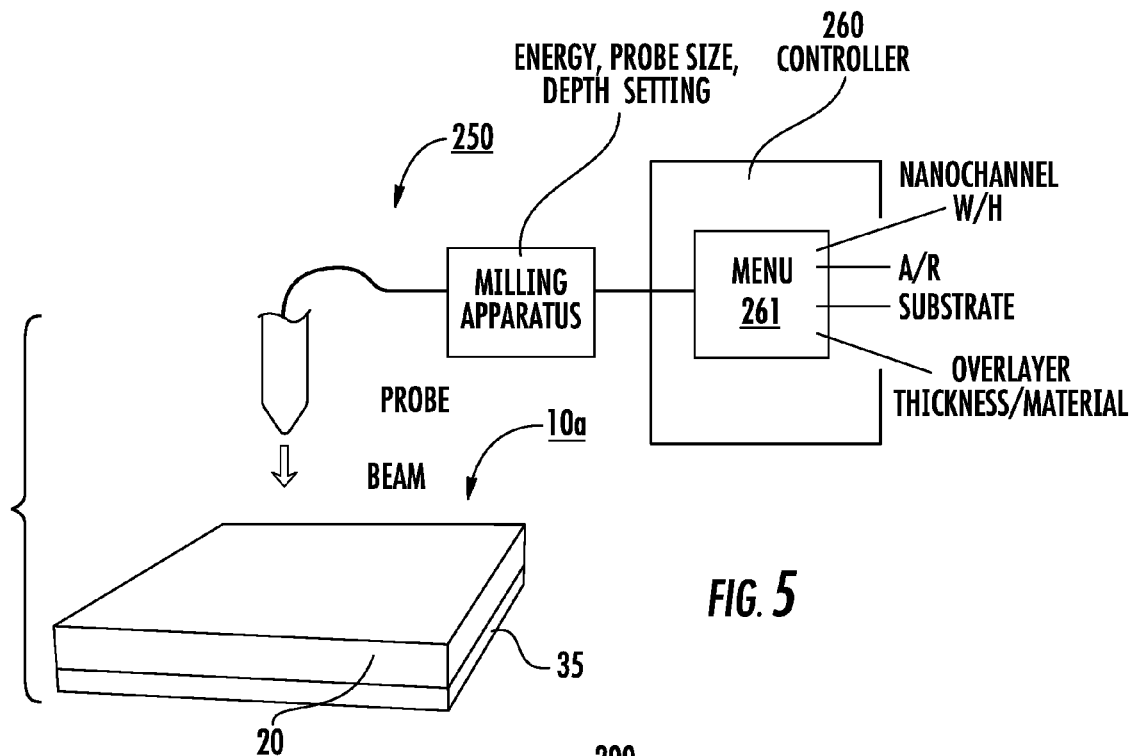
FIG. 5 is a schematic illustration of a milling apparatus with a controller configured to fabricate nanochannels according to embodiments of the present invention.

FIG. 5 illustrates that charged particle milling systems 250 can be configured with a controller 260 with an electronic menu 261 that allows the fabrication of different nanochannel configurations based on different substrate materials, different overlayer materials and/or thickness, correlated to operational parameters of the milling system 250 to automatically fabricate desired nanochannel configurations (with desired dimensions and/or ARs). The controller 260 can direct the system 250 to operate using a desired current (power), pattern, speed, beam size (probe), and the like to create the nanochannel configuration selected based on the substrate and overlayer in the fabrication assembly 10a being patterned. Examples of operational features correlated to overlayer material and thickness and substrate material are provided in the table below (measurements taken from SEM images). Such operation can allow convenient manufacturing of devices (e.g., semi-conductor molds, lab on chips) with desired small nanochannel sizes. It is contemplated that smaller probe sizes may be available in the future. Examples of commercially available milling systems include, for example, the Helios NanoLab DualBeam Instrument from the FEI Company, Hillsboro, Oreg.

sputtering yield (0.10 $\mu m^3$/nC for 30 keV $Ga^+$ ions at normal incidence) and ease of removal with chemical etchants. See, e.g., Orloff et al., M. J. *Vac. Sci. Technol. B* 1996, 14, 3759-3763. A commercial Chromium Mask Etchant (Transene Company, Inc.) was used. Nanochannels with relatively large critical dimensions (greater than ~30 nm in width) are milled by rastering the beam over a rectangular patterning region with a width approximately equal to the desired nanochannel width. The number of passes over the patterning region needed to achieve a nanochannel with the desired depth is dependent upon the ion beam current used and the metal film thickness. In fabricating a device, this depth setting can be verified and optimized by milling test features, cross-sectioning and imaging them, and adjusting the depth setting to achieve the desired dimensions.

Figures 6A, 6B, 6C:
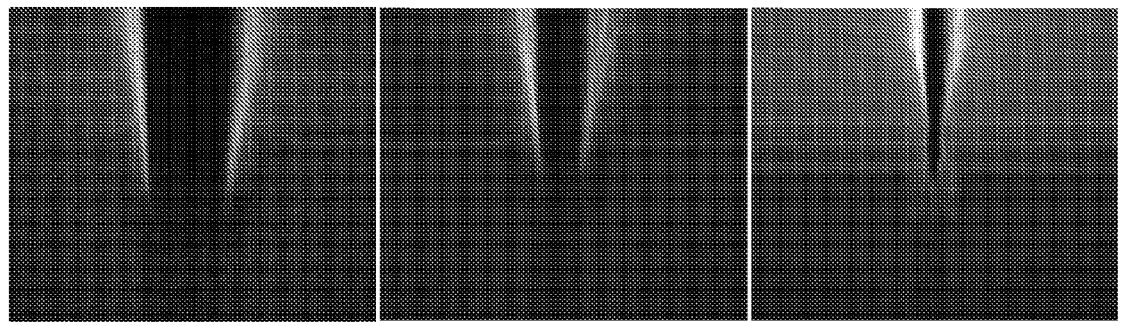
FIGS. 6a-6f are scanning electron microscope (SEM) images of nanochannel cross-sections milled through a 130 nm Cr (masking) overlayer into a quartz substrate (the specimens are tilted about 52 degrees with respect to the electron beam).
Figures 6D, 6E, 6F:
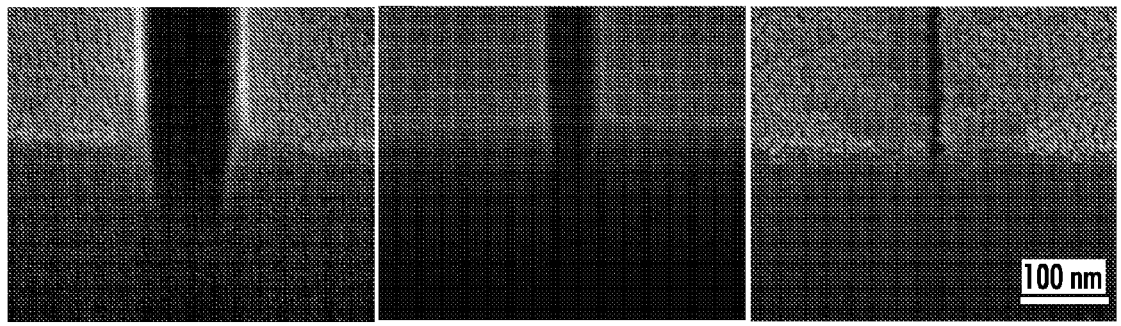

Smaller nanochannels can be milled by rastering the beam along a single line, with the channel width defined by the ion beam probe size and the metal film thickness. Using the smallest standard aperture (1.5 pA beam current, 7 nm probe diameter) available on a Helios NanoLab DualBeam Instrument (FEI Company) and milling through a 130-nm thick Cr film it has been possible to routinely mill channels with lateral dimension as small as 12-15 nm (FIGS. 6c and 6f). It is difficult to definitively characterize the cross-sectional shape of these channels but it is estimated at a roughly parabolic profile from the SEM images of the FIB-milled cross-sections. By simply increasing the Cr thickness to 300 nm it was possible to mill a channel that was less than 5-nm wide using

TABLE 1

NANOCHANNEL OPERATIONAL AND SIZE CORRELATION

| FIB PROBE SIZE (nm) | ION BEAM CURRENT (pA) | OVERLAYER MATERIAL | OVERLAYER THICKNESS (nm) | SUBSTRATE | NANOCHANNEL WIDTH (nm) |
|---|---|---|---|---|---|
| 7 | 1.5 | Cr | 150 | $SiO_2$ | 12-15 |
| 7 | 1.5 | Cr | 185 | $SiO_2$ | 10-12 |
| 7 | 1.5 | Cr | 245 | $SiO_2$ | 7-9 |
| 7 | 1.5 | Cr | 310 | $SiO_2$ | 3-5 |
| 13 | 9.7 | Cr | 130 | $SiO_2$ | 18-20 |
| 19 | 48 | Cr | 130 | $SiO_2$ | 27-29 |
| 7 | 1.5 | Al | 150 | Si | 18-20 |
| 7 | 1.5 | Al | 280 | Si | 12-15 |
| 17 | 28 | Al | 150 | Si | 35-38 |
| 7 | 1.5 | Pt | 70 | Si | 20-22 |
| 13 | 9.7 | Cr | 130 | PDMS | 20-22 (before relaxation) |

The present invention is explained in greater detail in the following non-limiting Examples.

EXAMPLES

Figure 7:
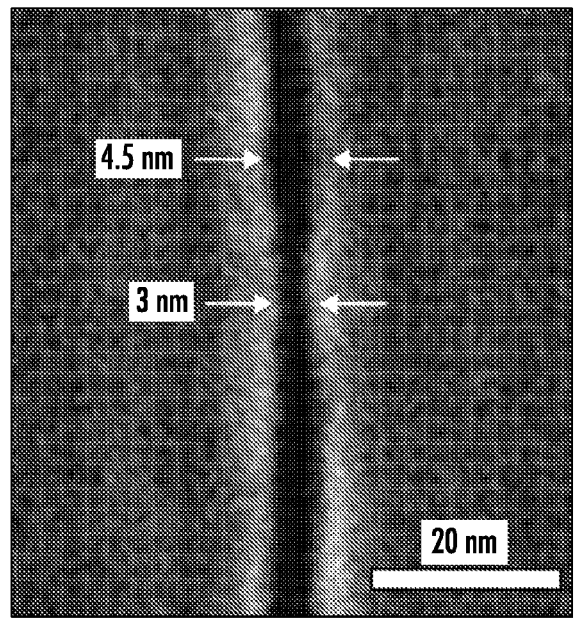
FIG. 7 is a top view of an SEM image of a sub 5 nm wide channel milled into a quartz substrate through a 300 nm Cr layer.

FIGS. 6a-6f illustrate exemplary nanochannels milled into a quartz substrate through a 130-nm thick Cr film using an ion beam probe with a beam current of 50 pA and diameter (FWHM) of 20 nm. The nanochannels milled in this fashion have roughly square cross-sections with near vertical (7-10° side walls. FIGS. 6a-c are SEM images of cross-sections taken before Cr film removal and FIGS. 6d-f are SEM images taken after Cr film removal. FIGS. 6a and 6d correspond to a 100 nm×100 nm channel, FIGS. 6b and 6e correspond to a 50 nm×50 nm channel. FIGS. 6c and 6f correspond to a 12 nm by 12 nm channel. This strategy has primarily been developed for the fabrication of nanochannels in quartz substrates as components in lab-on-a-chip devices. In this case, a chromium film was used as the conducting and masking layer. Chromium is well suited for this application given its low the same ion beam conditions (FIG. 7). Indeed, at a minima, the width was about 3 nm. Further systematic studies to ascertain the smallest obtainable channel dimensions are currently underway. The use of different (e.g., thicker or different material) overlayers and/or smaller FIB probe sizes is expected to push the ultimate dimensions to still smaller sizes.

The total milling time typically increases with decreasing ion beam current and increasing metal film thickness. Consequently, under the conditions used to achieve nanochannels with critical dimensions in the 5-15 nm range, channel length may be limited to approximately 10 microns, without stitching procedures. This is expected to be sufficiently long for many anticipated applications and longer milling times (and consequently longer channels) would be possible if compensation is made for sample drift. See, e.g., Holzer et al., *J. Microsc.* 2004, 216, 84-95.

Figure 8A:
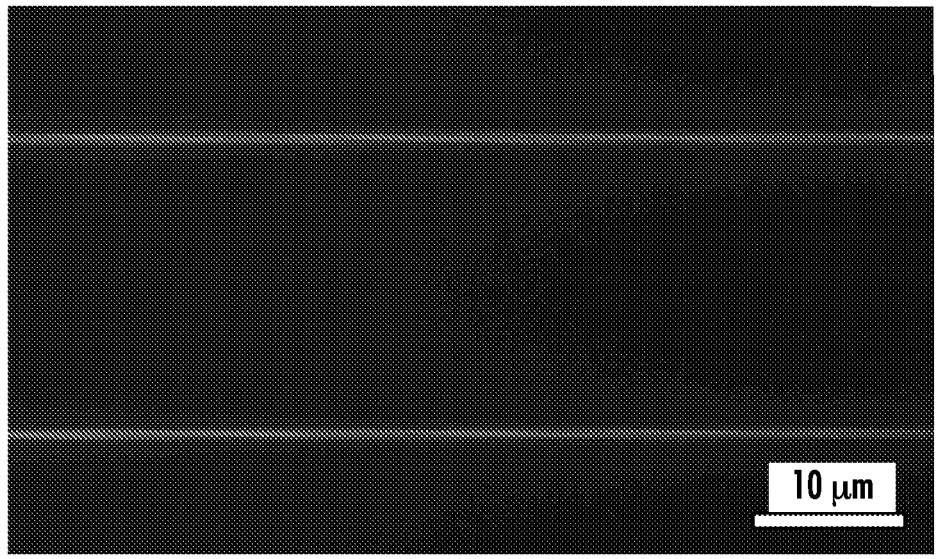
FIG. 8a is a fluorescence micrograph of a device with 30 nm nanochannels filled with 2 mM fluorescein dye.

These FIB-milled nanochannels are useful for nanofluidic experiments when sealed to form a fluidic network. This can be achieved in quartz devices by fusion bonding of a quartz cover plate to the photolithographically and ion beam patterned substrate after the Cr film has been removed. The substrate and cover plate are cleaned using Nano-Strip™ 2× stabilized piranha solution (Cyantek Corporation), their surfaces are activated in an oxygen plasma (Harrick Plasma, 18 W, 10 min), and then they are brought into contact, forming a reversible bond. The bonding is made permanent by heating the device to 900° C. in a furnace and holding at this temperature for >10 hrs. After bonding, the micro- and nanochannels can be filled with an aqueous solution of fluorescent dye (2 mM fluorescein) and imaged using fluorescence microscopy to verify that the channels are open and continuous and the bonding is defect free. FIG. 8a shows a fluorescence micrograph of nanochannels with a 30 nm×30 nm cross-sectional area in such an experiment.

Figure 8B:
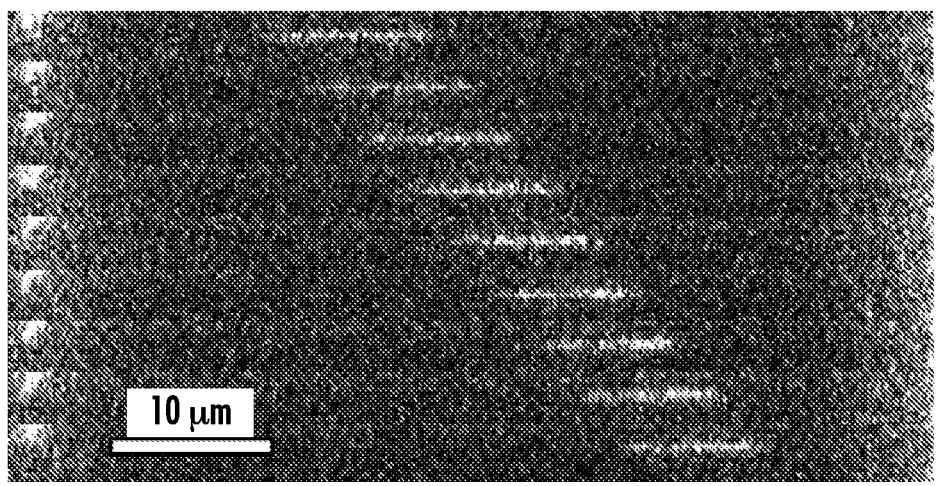
FIG. 8b is a series of frames recorded during the translocation of a single molecule of fluorescently stained λ-phage DNA through a 50 nm channel (a frame was collected about every 3 ms).

The quality of the nanochannel devices that are fabricated as described above are also evidenced by their utility in single molecule studies of DNA transport. In these experiments, fluorescently-stained double-stranded DNA molecules are electrophoretically driven through FIB-milled nanochannels of various sizes. FIG. 8b shows individual frames (a frame can be obtained about every 3 ms) from a recorded time series of the transport of a single molecule of fluorescently stained λ-phage DNA through a 50-1 µm long nanochannel with a 50 nm×50 nm cross-sectional area. The excellent operating characteristics of these nanofluidic devices can allow DNA molecules to be transported smoothly through FIB-milled nanochannels as small as 15 nm×15 nm with little evidence of adhesion. A constant electrophoretic mobility is observed over field strengths ranging from 200-25000 V cm$^{-1}$. Experiments can be run for several hours before the accumulation of DNA fragments (or solution impurities) on the nanochannel walls deleteriously affects device performance. These characteristics are indicative of nanochannels with extremely low surface roughness, in contrast to nanochannels or nanoslits fabricated using RIE that can exhibit high surface roughness. See, e.g., Salieb-Beugelaa et al., *Nano Lett.* 2008, 8, 1785-1790; Strychalski et al. *Macromolecules* 2008, 41, 7716-7721; and Haneveld et al., *J. Micromech. Microeng.* 2003, 13, S62-S66. Once a device is contaminated it can be effectively cleaned by filling the micro- and nanochannels with a 10% sulfuric acid solution (or other suitable cleaner) and typically allowing the device to sit overnight, followed by thoroughly rinsing the channels with water. Prototype devices have been used in the research laboratory for over 1 year with no observable change in performance.

Figure 9A:
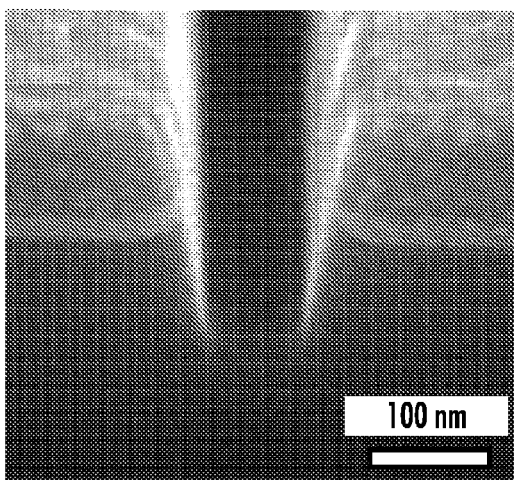
FIGS. 9a-9f are SEM images of nanochannels milled in Si substrates.
Figure 9B:
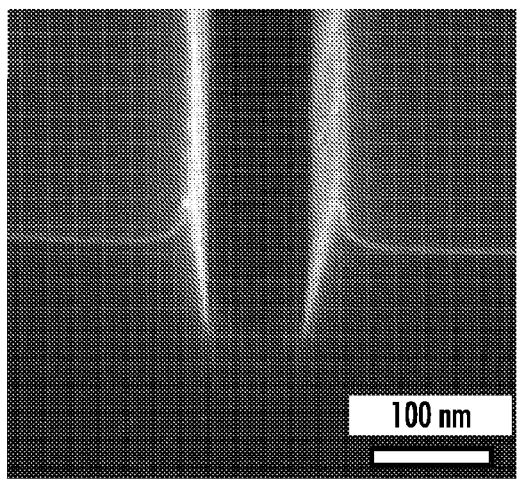
Figure 9C:
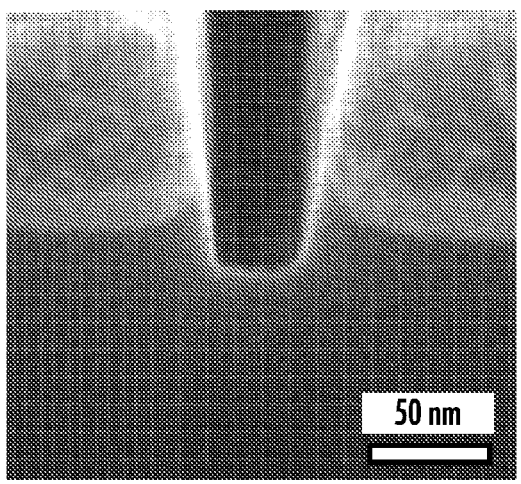
Figure 9D:
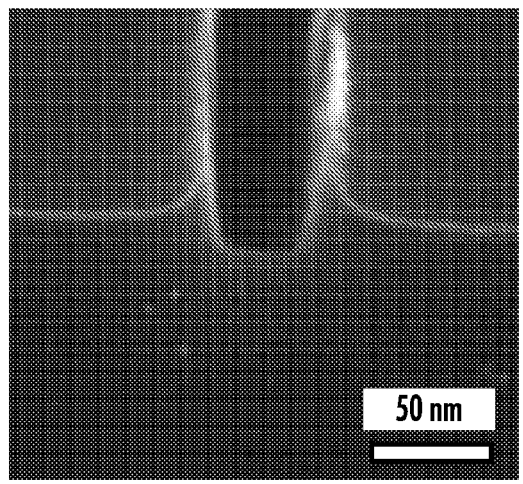
Figure 9E:
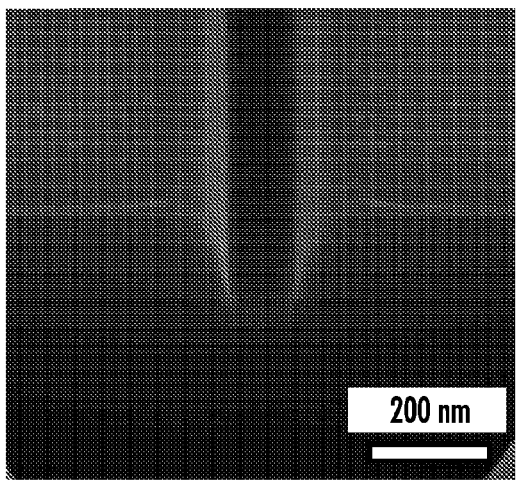
Figure 9F:
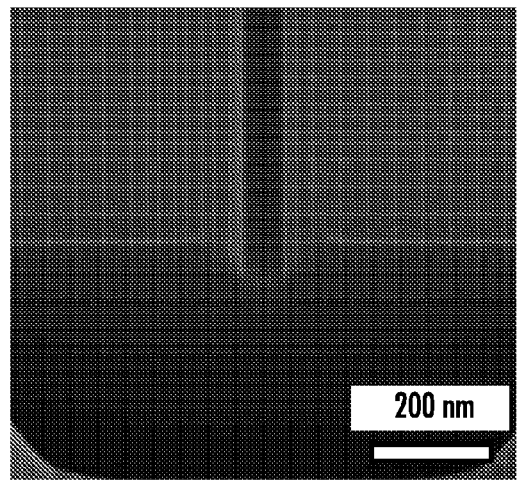

In addition to the fabrication of nanochannels in quartz, this method is readily transferable to other substrate materials, both hard and soft. Nanochannels were milled in Si(100) substrates through a 150-nm thick Al film. Aluminum, with a sputtering yield of 0.30 µm$^3$/nC, is not as effective as a masking layer as chromium. See, e.g., Orloff et al., *J. Vac. Sci. Technol. B* 1996, 14, 3759-3763. It was selected because it does not as readily form a silicide upon ion irradiation as Cr does and because the Al etching solution (PAN etch, 16:2:1:1 $H_3PO_4:H_2O:CH_3COOH:HNO_3$) is compatible with Si. See, e.g., Nakayama et al., *Microelectron. Eng.,* 86, 1718-1721. FIG. 9 shows SEM images of nanochannel cross-sections immediately after milling (FIGS. 9a and 9c) and after Al removal (FIGS. 9b and 9d). Although a metal film is not required to dissipate charge with semiconducting Si, the use of one yields nanochannels with a more uniform shape and smaller ultimate dimensions than can be achieved by milling directly into a Si substrate. This is made evident by comparing FIGS. 9e and 9f showing nanochannels milled directly into Si with those images of nanochannels milled through the Al film (FIGS. 9b and 9d). The nanochannels shown in FIGS. 9b and 9e and those shown in FIGS. 9d and 9f were milled with similar ion beam parameters, respectively.

Figure 10A:
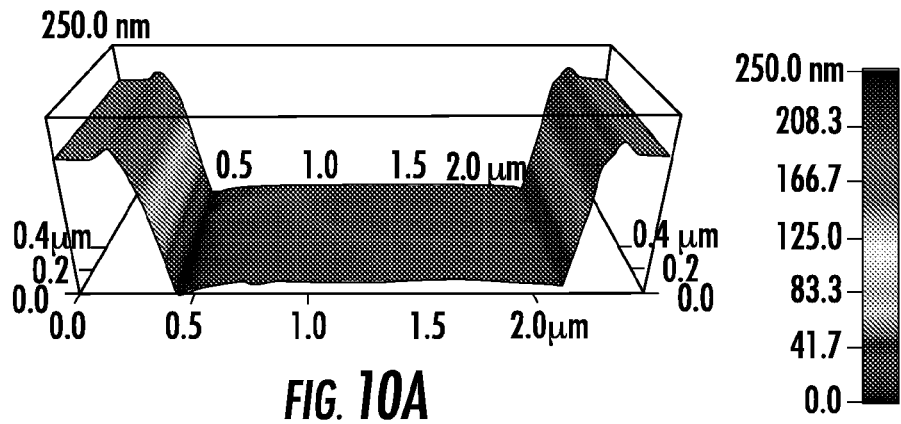
FIGS. 10a and 10b are AFM (atomic force microscopy) profiles of a 2 μm wide feature milled into an Si substrate.
Figure 10B:
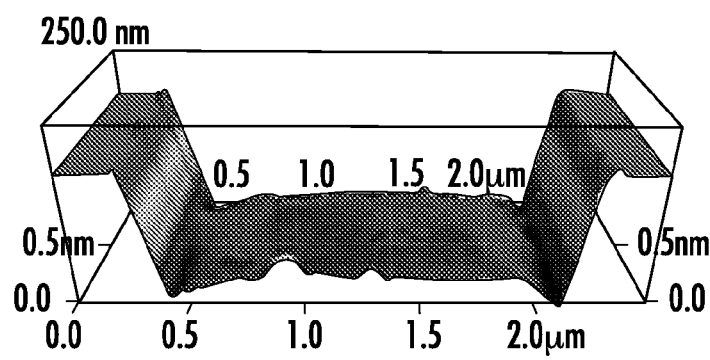
Figure 10C:
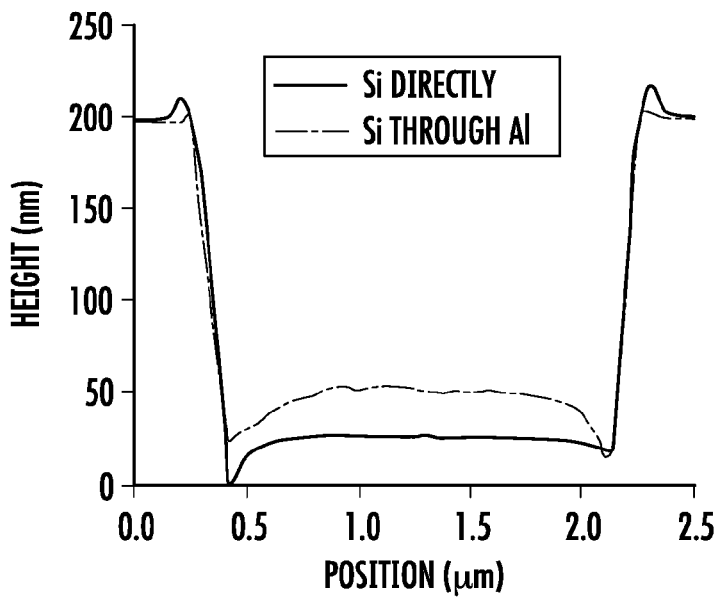
FIG. 10c is a graph (height, m) vs. position μm of line profiles obtained by averaging lines along the three dimensional profiles of FIGS. 10a and 10b.

Furthermore, the surface adjacent to a feature milled directly into a Si substrate is significantly deformed while the surface near a feature milled through an Al film has been protected. FIGS. 10a-10b shows representative atomic force microscopy (AFM) profiles of 2 µm wide features milled into a Si substrate (MFP-3D atomic force microscope, Asylum Research). The regions are milled into a Si substrate directly (FIG. 10a) or through a 150-nm thick Al film (FIG. 10b). In FIG. 10c these data are reduced to line profiles by averaging along the 1-µm length of the three-dimensional profiles (ca. 170 individual lines per profile). The protuberance observed along the edges of the feature milled directly into the Si substrate averages about 15 nm in height, consistent with observations in previous studies. See, e.g., Lugstein et al., *Appl. Phys. A* 2003, 76, 545-548; and Li et al., *Nanotechnology* 2003, 14, 220-223. In contrast, the Al film appears to be effective in protecting the top Si surface from redeposition and irradiation-induced swelling. The edges of the feature milled through the Al film are slightly raised (~4 nm). There is some lateral scattering of Ga$^+$ ions into the material and the presence of the Al film may be ineffective in preventing material damage resulting from such collisions.

While channels can generally be milled directly into semiconductor substrates, the characteristics of these channels are not ideal. As shown, the top edges of the channels are rounded, an effect due to milling by the peripheries of the ion beam, which has a Gaussian spatial flux distribution. The Gaussian distributed ion beam also limits the spatial resolution of the channels and results in a large variance in the nanochannel width. Also, when milling relatively shallow channels, ridges are known to form along the edges of the channel due to implantation-induced substrate amorphization. See, e.g., Lugstein et al., Appl Phys. A 2003, 76, 545-548 and Li et al., Nanotechnology 2003, 14, 220-223. This effect is expected to reduce the sealing efficiency during coverplate bonding. In contrast, the channels milled through an Al masking layer do not show the dramatic rounding of the channels milled directly in Si and the top surface of the substrate is highly planar. The (two-fold) improvement in the achievable channel resolution, in combination with the improved morphology for nanofluidic devices, illustrates the advantage of using a thick (metallic) masking layer.

Figure 11A:
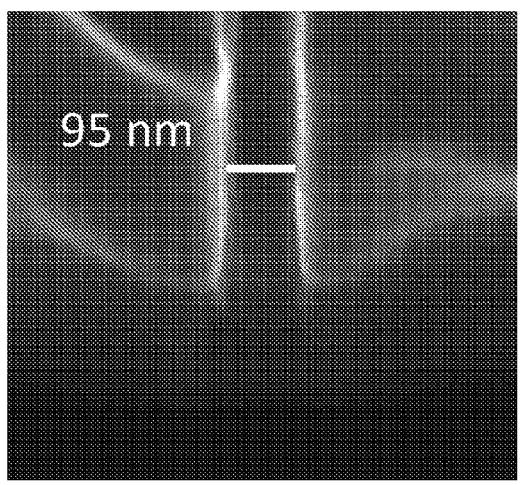
FIGS. 11a and 11b are SEM images of a flexible substrate with a milled nanochannel.
Figure 11B:
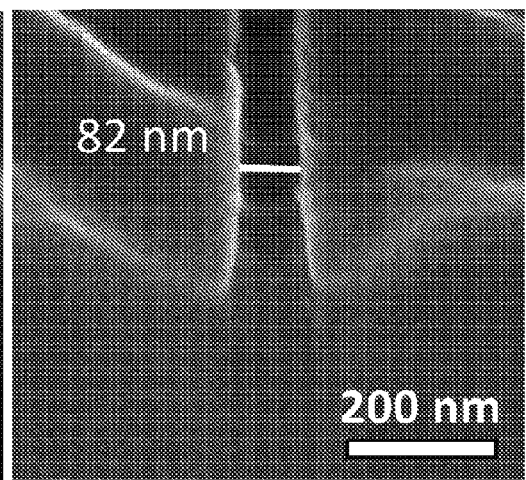

Finally, the use of this methodology for the patterning of soft materials was investigated, in this case polydimethylsiloxane (PDMS, Sylgard® 184, Dow Corning Corporation). In an attempt to leverage PDMS's elastomeric properties, a 130-nm thick Cr film was deposited and FIB milling performed on a piece of 1-mm thick PDMS that was stretched ~20% on a custom built specimen mount. The nanochannels were oriented such that the channel length and width were perpendicular and parallel to the stretch direction, respectively. After milling and while the sample was still stretched, the Cr film was removed and a thin (4 nm) Cr film was deposited to dissipate charge during SEM imaging. An SEM image of the nanochannel in the stretched PDMS substrate, having a width of 95 nm, is shown in FIG. 11a. The 4-nm Cr film is then removed, the sample is relaxed, a new 4-nm Cr film is deposited and the sample is re-imaged (FIG. 11b). The nanochannel width is now 82 nm, a 14% decrease commensurate with the 17% decrease in the bulk dimensions of the PDMS upon relaxation. This demonstrates the broad applicability of the milling strategy to a wide range of substrate materials and suggests a method for extending the ultimate dimensions accessible using (FIB) milling/patterning by taking advantage of the materials properties of substrates and masking layers.

The unique properties of FIB milled nanochannels in glassy substrates provide a further means of controlling or adjusting the nanochannel dimensions.

After removal of the metal masking film from quartz (glassy) substrates, the FIB-milled nanochannels can be transformed to relatively wide and very shallow nanoslits by heating the substrates to a high temperature that is lower than the bulk glass transition temperature of the substrate material. In the case of quartz, this can be achieved at temperatures as low as 850° C. despite the fact that quartz's annealing point is ~1200° C. See, e.g., Douville et al., *Anal. Bioanal. Chem.* 2008, 391, 2395-2409. The presence of additives in quartz results in a shift of the glass transformation range to lower temperatures. In the case of FIB milling, $Ga^+$ ions that are implanted into the quartz to depths of ~30 nm are responsible for a lowering of this transformation range in the region local to the milled channel (due to the impurities). The surrounding region, in which $Ga^+$ ions are not implanted, exhibits a higher viscosity at the annealing temperature and prohibits the total melting of the top surface and loss of the milled feature. What occurs is material flow within the region of $Ga^+$ implantation that minimizes surface strain by minimizing the curvature of the channel. At sufficiently high temperatures this material is fluidized while the bulk substrate material remains rigid. The result is a minimization of the radius of curvature of the nanochannel (and thus its surface energy), producing a wide and shallow channel with an extremely smooth and regular surface (FIG. 12*b*). FIGS. 12*a* and 12*b* show a nanochannel in a quartz substrate after it is heated at 700° C. (12*a*) and then heated again at 850° C. (12*b*). It is envisioned that these defect-free nanoslits will allow studies of molecules confined in environments comparable to their molecular dimensions. FIGS. 12*a* and 12*b* are SEM images of a nanochannel milled in quartz through a 130-nm Cr film after (12*a*) heating to 700° C. and (12*b*) 850° C. In FIG. 12*a*, the channel has width× depth dimensions of 20 nm×20 nm. FIG. 12*b* shows the channel with a width of 80 nm and depth at the center of the channel of about 6 nm. Sealing these nanochannels can provide "nanoslits" with slit heights that approach single nanometer dimensions.

Figure 13:
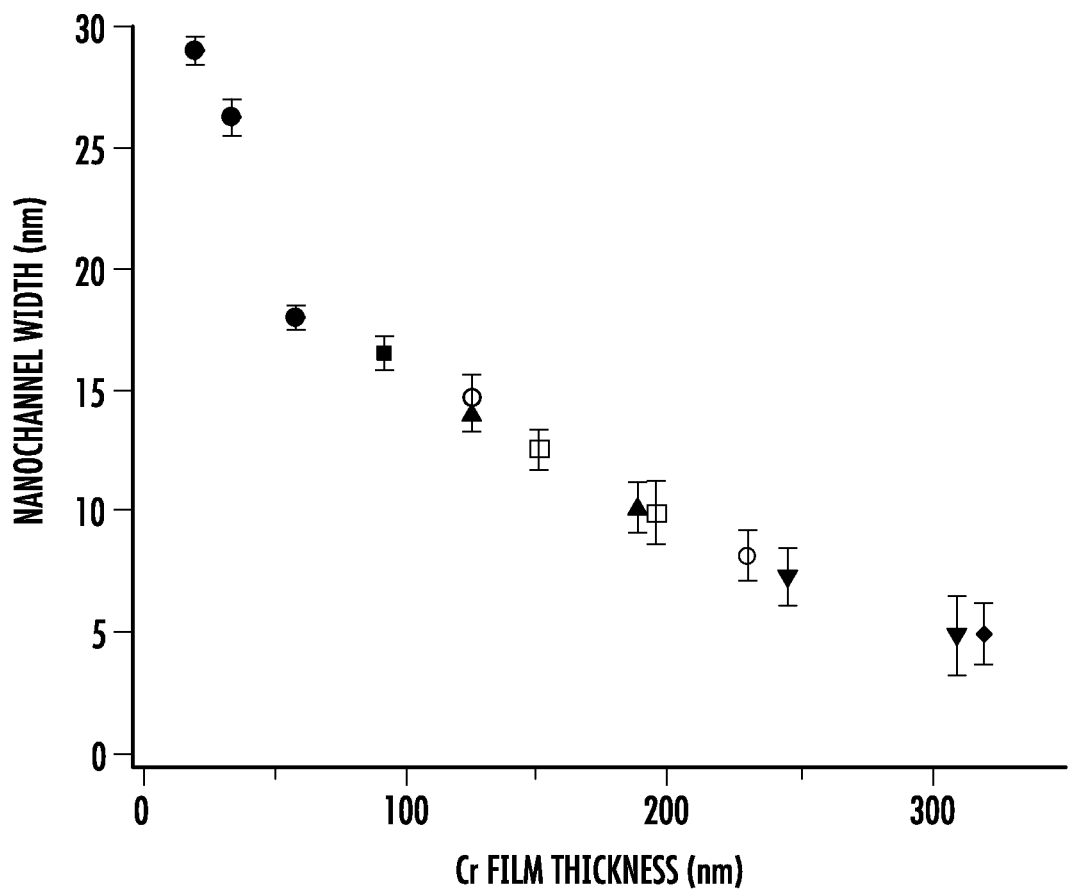
FIG. 13 is a graph of FIB milled nanochannel width (nm) versus Cr film thickness (nm) according to embodiments of the present invention.

FIG. 13 is a graph of nanochannel width (nm) versus Cr film thickness (nm). This graph illustrates the effect of Cr film thickness on the width of nanochannels FIB milled into a quartz substrate using a 1.5 pA ion beam current (nominal). Different markers represent samples that were milled during seven different sessions on the instrument. Each value was determined from width measurements at multiple locations along at least three different channels (n=20 for each point).

In summary, the use of a sufficiently thick overlayer can offer the advantages of smaller nanochannel dimensions and smoother surfaces along the nanochannel edges. These nanochannels can be incorporated into fluidic devices by interfacing them to microfluidic channels and by sealing the top surface of the channels with a cover plate. This methodology can be applied to both hard and soft materials of potential utility in nanofluidic technologies. The channels obtained are continuous with little variance in their dimensions. Nanochannels with sub-5 nm critical dimensions have been formed and fluidic experiments have been run in sub-10 nm nanochannels. This is important to note because the smallest sized features fabricated using other methods have generally not been demonstrated as components of working devices. Moreover, the described methodology may have application to the formation of molds used in nanoimprint lithoghraphy, a potential next generation lithography technique for the microelectronics industry.

Fluidic devices containing nanochannels with the critical dimensions and tolerances afforded by this new fabrication technique are expected to be of great utility for a number of applications. These include extremely sensitive chemical sensing technologies, physical measurements of single confined molecules, separations, biological assays, and genomic sequencing technologies. Because the FIB milled nanochannels and nanoslits are easily interfaced with other fluidic components on a single chip their use can be integrated with other technologies such as flow injection, separations in microfluidic channels, and single cell lysis.

The described nanofabrication methodology has application to microelectronics and nanofluidics technology. Microelectronics applications include the formation of molds for nanoimprint lithography.

Nanofluidic implementations with nanochannels of these critical dimensions and quality are well-suited for a number of applications including single molecule detection and identification, confinement and manipulation of biopolymers, biological assays, restriction mapping of polynucleotides, DNA sizing, physical methods of genomic sequencing, and fundamental studies of the physics of confinement.

The nanochannels described herein are believed to have cross-sectional areas that are one to two orders of magnitude smaller than any previously reported FIB milled features. This capability is enabled by milling the channels into the substrate through a relatively thick high quality conductive material (e.g., metal film) deposited on the top surface of the substrate. This film acts as a masking layer, confining the lateral extent of the FIB milled channel. The presence of the metal film also prevents the formation of a ridge along the channel edges resulting from redeposition of sputtered material and protects against penetration of ions into the surface of the substrate and consequent damage.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A method of forming at least one nanochannel, comprising:
   providing a substrate having a thick single overlayer or a thick multi-layer overlayer;
   milling at least one channel through the overlayer into the substrate; and
   removing the overlayer to
   expose at least one nanochannel in the substrate in response to the milling and removing steps.

2. The method of claim 1, wherein the milling at least one channel through the overlayer into the substrate is carried out to mill a plurality of channels through the overlayer and into the substrate before the removing step, wherein the removing step exposes a plurality of nanochannels as the at least one nanochannel, and wherein the nanochannels have an average width and/or depth that is less than about 10 nm.

3. The method of claim 1, wherein the milling and removing steps are carried out to form a plurality of nanochannels in the substrate as the at least one nanochannel, the nanochannels having a width and/or depth that is less than about 5 nm.

4. The method of claim 1, wherein the milling and removing steps are carried out to form a plurality of nanochannels in the substrate, the nanochannels having a depth that is between about 1 nm to about 3 nm and/or a width that is between about 1 nm to about 10 nm.

5. The method of claim 1, wherein the substrate is a substantially planar substrate and comprises a soft material having a Young's Modulus that is between about 0.1-3000 MPa.

6. The method of claim 1, wherein the substrate is a substantially planar substrate and comprises a substantially rigid material.

7. The method of claim 1, wherein the overlayer comprises a conductive material with a low sputtering rate of between about 0.05 to about 0.5 μm$^3$/nC or less.

8. The method of claim 1, wherein the overlayer comprises a metallic film.

9. The method of claim 1, wherein the overlayer is between about 50 nm and 500 nm thick.

10. The method of claim 1, wherein the milling step is carried out using focused ion beam (FIB) milling.

11. The method of claim 1, wherein the substrate comprises an elastomeric material, and wherein the method further comprises:
 stretching the elastomeric material substrate during the milling step; then
 releasing the elastomeric material substrate to a non-stretched configuration to reduce a width dimension of the at least one nanochannel.

12. The method of claim 11, wherein the stretching is carried out to stretch the elastomeric material between about 10-30%.

13. The method of claim 1, wherein the at least one nanochannel has a smooth inner surface.

14. The method of claim 1, wherein the overlayer has multiple stacked layers, including a first layer attached to the substrate of a first material, and a second layer of a different second material attached to and residing above the first layer, the second layer comprising a conductive film.

15. The method of claim 1, wherein the substrate comprises an electrically insulating material and the overlayer comprises a metallic film.

16. The method of claim 1, wherein the overlayer comprises an electrically insulating material and the substrate comprises a conductive material.

17. The method of claim 1, further comprising heating the substrate after the removing step to a temperature sufficient to cause at least a lower portion of the at least one nanochannel to increase in width while decreasing the depth of the at least one nanochannel.

18. The method of claim 1, wherein the substrate comprises quartz, wherein the milling step is carried out using focused ion beam (FIB) milling configured to deposit Ga$^+$ ions in the quartz proximate the at least one nanochannel, and wherein the method further comprises heating the substrate to a temperature between about 850 degrees Celsius and less than 1200 degrees Celsius to cause the quartz proximate the at least one nanochannel to flow within a region associated with the Ge ions to create a respective nanochannel having a wider channel dimension and a more shallow depth dimension.

19. A method of forming a fluidic analysis device, comprising:
 providing a substrate having a single sacrificial overlayer or a thick multi-layer sacrificial overlayer, wherein the sacrificial overlayer has a thickness that is between 50 nm and 500 nm;
 focused ion beam (FIB) milling through the overlayer into the substrate to form a plurality of channels through the overlayer and into the substrate with a cumulative width and/or depth dimension associated with the overlayer and substrate that is greater than 50 nm; and
 removing the sacrificial overlayer from the substrate to expose nanochannels in the substrate formed by the FIB milling through the overlayer.

20. The method of claim 19, wherein the sacrificial overlayer is bonded to the substrate for the milling step and comprises a conductive material with a low sputtering rate that is between 0.05 to 0.5 μm$^3$/nC.

21. The method of claim 19, wherein the FIB milling is carried out using a Ga$^+$ beam.

22. The method of claim 19, further comprising attaching a cover to the substrate after the removing step to provide a fluidic analysis device for DNA transport studies.

23. The method of claim 19, wherein the nanochannels in the substrate have a width that is between one or more of the following:
 3-5 nm, 7-9 nm, 10-12 nm, 12-15 nm, 18-20 nm, 20-22 nm, 27-29 nm, or 35-38 nm.

* * * * *

UNITED STATES PATENT AND TRADEMARK OFFICE
CERTIFICATE OF CORRECTION

PATENT NO.        : 9,139,426 B2                                    Page 1 of 1
APPLICATION NO.   : 13/824767
DATED             : September 22, 2015
INVENTOR(S)       : Ramsey et al.

It is certified that error appears in the above-identified patent and that said Letters Patent is hereby corrected as shown below:

In the Specification:
Column 6, Line 12: Please correct "He" to read -- $He^+$ --
Column 8, Line 60: Please correct "nC, For a" to read -- nC. For a --
Column 9, Line 5: Please correct "man be thicker" to read -- may be thicker --
Column 9, Line 36: Please correct "1.50 $nm^3$/nC" to read -- 1.50 $\mu m^3$/nC --
Column 11, Line 57: Please correct "(7-10°"" to read -- (7-10°) --
Column 13, Line 24: Please correct "50-1 µm" to read -- 50 µm --

In the Claims:
Column 16, Claim 1, Lines 56-57: Please correct the spacing in the sentence below:
    "removing the overlayer to
    expose at least one nanochannel in the substrate in response"
to read as a continuous sentence as follows: -- removing the overlayer to expose at least one nanochannel in the substrate in response --
Column 18, Claim 18, Line 14: Please correct "Ge ions" to read -- $Ga^+$ ions --

Signed and Sealed this
Twelfth Day of July, 2016

Michelle K. Lee
*Director of the United States Patent and Trademark Office*